(12) United States Patent
Machill et al.

(10) Patent No.: US 12,727,964 B2
(45) Date of Patent: Sep. 8, 2026

(54) GLASS TAG TRANSPONDER INSTALLATION/RETROFITTING FOR MOTOR CABLE

(71) Applicant: Aesculap AG, Tuttlingen (DE)

(72) Inventors: Martin Machill, Rietheim-Weilheim (DE); Frederick Lenzenhuber, Tuttlingen (DE); Ralf Pfister, Trossingen (DE); Roland-Alois Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/576,992

(22) PCT Filed: Jul. 6, 2022

(86) PCT No.: PCT/EP2022/068791
§ 371 (c)(1),
(2) Date: Jan. 5, 2024

(87) PCT Pub. No.: WO2023/280942
PCT Pub. Date: Jan. 12, 2023

(65) Prior Publication Data

US 2025/0082433 A1 Mar. 13, 2025

(30) Foreign Application Priority Data

Jul. 6, 2021 (DE) ..................... 10 2021 117 413.9

(51) Int. Cl.
*A61B 90/92* (2016.01)
*A61B 90/98* (2016.01)
*G06K 19/077* (2006.01)

(52) U.S. Cl.
CPC .............. *A61B 90/98* (2016.02); *A61B 90/92* (2016.02); *G06K 19/0772* (2013.01); *G06K 19/07758* (2013.01)

(58) Field of Classification Search
CPC .... A61B 90/98; A61B 90/92; G06K 19/0772; G06K 19/07758
(Continued)

(56) References Cited

U.S. PATENT DOCUMENTS 9,940,569 B2 4/2018 Lynch et al.
2004/0117515 A1 6/2004 Sago et al.
(Continued)

FOREIGN PATENT DOCUMENTS

CN 204229000 U 3/2015
DE 19802462 A1 8/1999
(Continued)

OTHER PUBLICATIONS

Search Report received in German Application No. 10 2021 117 413.9 dated Jun. 3, 2022, with translation, 10 pages.
(Continued)

*Primary Examiner* — Michael G Lee
*Assistant Examiner* — David Tardif
(74) *Attorney, Agent, or Firm* — Christopher A. Rothe; CM Law

(57) ABSTRACT

A medical instrument includes at least one internal electrical energy load, preferably an electric motor, a cable plug, and a motor cable, which connects the medical instrument to a cable-side end of the cable plug to supply the at least one energy load. The cable plug has a pole-side end for insertion into a jack preferably located on a control unit. A glass tag can be or is inserted into or attached to the pole-side end without an application of force and is provided and designed to be readable by an antenna located on the jack. An adapter component is configured for retrofitting a jack of a control unit. A system includes a medical instrument, a motor cable, a cable plug and a control unit having a jack.

10 Claims, 4 Drawing Sheets

(58) Field of Classification Search
USPC .......................................................... 235/492
See application file for complete search history.

(56) References Cited

U.S. PATENT DOCUMENTS

| | | | | |
|---|---|---|---|---|
| 2008/0318477 | A1 | 12/2008 | Standke | |
| 2019/0298267 | A1 | 10/2019 | Warner et al. | |
| 2021/0038239 | A1 | 2/2021 | Gatineau et al. | |
| 2022/0108144 | A1 * | 4/2022 | Matsumoto | A61B 90/98 |
| 2022/0287797 | A1 * | 9/2022 | Hoegerle | A61B 90/98 |
| 2024/0081945 | A1 * | 3/2024 | Hoegerle | A61B 90/08 |
| 2025/0082433 | A1 * | 3/2025 | Machill | G06K 19/07758 |

FOREIGN PATENT DOCUMENTS

| | | | |
|---|---|---|---|
| DE | 10351773 | A1 | 6/2004 |
| DE | 20005006373 | U1 | 10/2006 |
| DE | 102005044918 | A1 | 2/2007 |
| DE | 102005046040 | A1 | 4/2007 |
| DE | 102007017407 | A1 | 10/2008 |
| DE | 102013111376 | A1 | 4/2015 |
| DE | 102018101221 | A1 | 7/2019 |
| DE | 102019122349 | A1 | 2/2021 |
| EP | 2087850 | A2 | 8/2009 |
| EP | 2043547 | B1 | 9/2011 |
| EP | 3146477 | A1 | 3/2017 |
| EP | 3323375 | A1 | 5/2018 |
| WO | 2015177490 | A1 | 11/2015 |
| WO | 2021032782 | A1 | 2/2021 |
| WO | 2021069662 | A1 | 4/2021 |

OTHER PUBLICATIONS

Search Report received in International Application No. PCT/EP2022/068791 dated Jan. 2, 2023, with translation, 9 pages.
Written Opinion received in International Application No. PCT/EP2022/068791 dated Jan. 2, 2023, with translation, 21 pages.

* cited by examiner

GLASS TAG TRANSPONDER INSTALLATION/RETROFITTING FOR MOTOR CABLE

CROSS-REFERENCE TO RELATED APPLICATIONS

This application is the United States national stage entry of International Application No. PCT/EP2022/068791, filed on Jul. 6, 2022, and claims priority to German Application No. 10 2021 117 413.9, filed on Jul. 6, 2021. The contents of International Application No. PCT/EP2022/068791 and German Application No. 10 2021 117 413.9 are incorporated by reference herein in their entireties.

FIELD

The present disclosure relates to a medical instrument comprising at least one internal electric energy consumer, preferably an electric motor, a cable plug and a motor cable, which connects the medical instrument to a cable-side end/end portion of the cable plug for supplying the at least one energy consumer, wherein the cable plug has a pole-side end for being plugged into a plug socket, which is preferably arranged on a control device. Furthermore, the present disclosure relates to an adapter component for retrofitting a plug socket of a control device and to a system comprising a medical instrument, a motor cable, a cable plug and a control device with a plug socket.

BACKGROUND

Due to the increasingly important issue of tracking, tracing and life cycle management in the future, more and more medical products of all kinds, such as motor-driven drills, saws and motor cables etc., are being equipped with so-called passive transponders, preferably RFID or NFC. In particular, the already familiar design of the so-called glass tag is used.

The problem here is to install a glass tag, in particular an RFID glass tag, with a protective housing simply but securely and compactly and also as a retrofit on the products. For the retrofitting on products, this should not have to be reworked if possible, or only with very little effort.

Glass tags can also be understood as RFID tags and/or NFC tags. NFC is a sub-form of RFID technology. Thus, an NFC tag can also be used instead of an RFID tag according to the invention. Furthermore, the glass tag is preferably an RFID transponder for storing information associated with a specific object (in this case the medical/surgical instrument). This so-called 'identifier' can be individualized according to the requirements of the respective process. Preferably, the glass tag consists of:

- At least one microchip, preferably a few millimeters in diameter,
- at least one antenna, preferably in the form of a coil,
- at least one carrier or housing, the housing preferably being watertight and/or airtight and preferably protecting the transponder electronics from the environment,
- in the case of an active RFID tag, additionally at least one energy source, preferably a battery/accumulator or a capacitor.

Often only small wall thicknesses are available to accommodate the glass tag with a housing/protective housing on the product. This makes classic snap-on elements such as snap-on hooks almost impossible to implement. Certain instruments, such as motor-driven saws, are furthermore subject to high vibrations, meaning that even snap-on hooks are too delicate in this size and may break in the long term. So-called ring snap connections that snap into an instrument housing via a bead also have the disadvantage that a force is exerted on the glass tag during assembly or snapping in due to deformation of the housing with the glass tag, which in turn can destroy the glass tag during assembly.

Glass tags integrated into/attached to instruments are already known from the prior art. For example, EP 2 087 850 A2 discloses a transponder device and/or a housing for marking a surgical device, such as a metallic surgical instrument. Here it is provided to encompass a flexible strap, wherein the strap can enclose at least a part of a surgical device. Furthermore, a housing is provided that has a strap receiving cavity dimensioned to receive at least a portion of the strap in order to retain the strap to the housing and a transponder receiving cavity dimensioned to receive a transponder, wherein the transponder receiving cavity is spaced at least about 1 millimeter from any portion of the surgical instrument when the housing is attached to the surgical instrument via the strap.

EP 3 146 477 A1 discloses an RFID tag arrangement comprising a passive, metal-mounted RFID tag and a mounting element. The passive, metal-mounted RFID tag is arranged to transmit an HF signal. The mounting member is made of an electrically conductive material and comprises a base portion and at least one wall portion extending outward with respect to a first surface of the base portion. The at least one wall portion is configured to at least partially define a recess in which the RFID tag is received at least up to a portion of its height. The RFID tag is physically coupled to the base portion and the at least one wall portion. A surgical instrument to which an RFID tag assembly is attached is also provided.

Previous solutions of the prior art require a complex attachment directly as well as the retrofitting of the products by attachment by molding, gluing, press-fitting via force fit or ultrasonic welding. Both molding and gluing are complex processes and require appropriate preparation of the parts so that they are/will be free of grease and clean, for example. Press-fitting via force-fit is not permanently durable due to the setting of plastic.

In other words, some prior art solutions that offer tracking, tracing and tagging of the instruments involve the glass tags being inserted into holes or being glued onto the instruments, which significantly affects ergonomics and handling.

SUMMARY

Therefore, the object of the present disclosure is to attach or accommodate a glass tag with a protective housing to or in the product in a simple, safe and space-saving manner without forces acting on the glass tag during assembly.

Accordingly, the present disclosure relates to a medical (hand) instrument comprising at least one internal electric energy consumer, preferably an electric motor, a cable plug and a motor cable, which connects the medical instrument to a cable-side end/end portion of the cable plug for supplying the at least one energy consumer, wherein the cable plug has a pole-side end/end portion for being plugged into a plug socket, which is preferably arranged on an (external) control device, and wherein a glass tag is attachable in/to or attached in/to the pole-side end/end portion without applying force (i.e. force-free) and is provided and configured to be readable by an antenna arranged or attachable to the plug socket.

In other words, this means that a glass tag, preferably already accommodated in a protective housing, is attached to or inserted into the cable plug in such a way that it communicates/can communicate with an antenna arranged in or on it when inserted into a plug socket. It is preferable, among other things or alternatively, that an existing cable plug can be easily retrofitted with a glass tag. This type of installation or attachment has the advantage that reliability and signal amplification/receivability are also improved. It is also advantageous that medical treatment/cleaning is possible even when the glass tag is installed/attached with a tag's own protective housing. Furthermore, communication/(data) exchange between the motor cable and the control device is possible. For communication/(data) exchange with the control device, a preferably integrated antenna/reader antenna is placed in the area of the plug socket of the control device.

The advantage here is that retrofitting the motor cable with the glass tag is simple and cost-effective. This tag retrofit makes it possible to record all motor cable activities in connection with the application parts and handling in everyday clinical practice.

In other words, the medical (hand) instrument according to the disclosure has an internal electric motor or pneumatic motor and a power supply cable harness and possibly control cable harness, which is preferably fixedly (non-detachably) mounted on the instrument and has the cable plug at its free end. The cable plug has a plug-in portion at the end with a number of contact pins/poles and/or pneumatic connections arranged therein. Finally, an RFID tag or glass tag is provided, which is accommodated in a protective housing, which is preferably configured in the shape of a sleeve and is provided and dimensioned to be placed on the plug-in portion in a ring-like manner or which is preferably designed in the shape of a bunker or mound (in the manner of a zeppelin cockpit) and is provided and dimensioned to be formed, glued, soldered or welded directly to the outer side of the plug-in portion.

Preferably, the glass tag or the attachment/accommodation is demountable and/or exchangeable and configured for easy cleaning.

In other words, it is advantageous if the attachment or accommodation of the glass tag is configured such that the glass tag is demountable and/or exchangeable without damaging the medical instrument.

It is preferred if the glass tag is arranged in a color-coded ring/sleeve, wherein the color-coded ring surrounds the cable plug on the outside at the pole-side end (plug-in portion). In other words, it is provided that the glass tag is integrated into the already existing and necessary color-coded ring on the motor cable, which had previously been used for the maintenance date and is simply replaced during servicing and thus provided with a new date. For this purpose, the color-coded ring is given/has a suitable geometry to receive/integrate the glass tag.

It is advantageous if the color-coded ring is configured with a zeppelin cockpit in which the glass tag can be integrated. The size of the zeppelin cockpit is such that the glass tag can be received/accommodated in it. The zeppelin cockpit has a geometry that almost corresponds to the shape of the glass tag and is attached to the color-coded ring as a bulge/projection/elevation. After inserting the glass tag into the zeppelin cockpit, one front side of the glass tag points toward the pole-side end. The glass tag has good read-out properties on the front side.

Alternatively, it is advantageous if the glass tag is integrated in a ring which can be plugged onto the pole-side end.

It is preferred if the outer side of one half of the ring has a cuboid extension in which a tag holder is provided and configured, in which the glass tag is held. In other words, an attachable ring with an integrated glass tag is provided as an alternative embodiment. The advantage of this embodiment is that it is backward compatible and can be retrofitted, but is only compact to a limited extent. Furthermore, the attachable ring is removable.

It is advantageous if the glass tag is provided with a signal amplification plate that has at least one opening. The glass tag already has good readout properties at the front side and is reinforced at the side by a plate/signal amplification plate, so that readout with various readout devices from various directions is improved or possible. This means that the lasered date for the next servicing (ATS) can be transferred to the glass tag, or both can be present if required. Each opening in the signal amplification plate stands for an effective direction.

It is advantageous if the signal amplification plate is a flat plate, an L-shaped plate, a U-shaped plate or a tubular plate. In other words, in all embodiments, the signal amplification plate is arranged around or on the glass tag. For example, this may be a flat plate which has an opening and thus an effective direction. Another example is an L-shaped plate that surrounds two sides of the glass tag. Here, either a bent opening or two openings may be provided on each side of the L, so that the glass tag in combination with the signal amplification plate provides two effective directions. In another example, the signal amplification plate may be configured in a U shape and may have three openings in the circumferential direction, which represent three effective directions. Furthermore, a tubular signal amplification plate is also provided, which is equipped with various openings with corresponding effective directions.

It is preferred if the shape and the number or size of the at least one opening can be variably combined with one another.

Alternatively, it is preferred if the pole-side end has a plurality of plug-in locations, wherein only a part of the plurality of plug-in locations is occupied by pole plugs (contact pins) and the glass tag is inserted at least partially insertably in an unoccupied plug-in location. In other words, a free plug-in location in the plug is equipped with a glass tag according to the disclosure, integrated in a contact dummy (corresponds to the protective housing mentioned above).

In this embodiment, the glass tag may either be completely insertable in a plug-in location or protrudingly pluggable into a plug-in location. The advantage of the glass tag inserted in the plug-in location is that this embodiment is backward-compatible, retrofittable and compactly configured. Although the protrudingly plugged glass tag can be retrofitted and has a compact configuration, it is not backward compatible with existing control devices. Backward compatibility or downward compatibility refers to the usability of newer or extended versions of a technical object or standard under the application conditions of an earlier version.

In summary, the two alternative embodiments described above require a compact antenna inside the plug socket for future control devices, compared to the plug-in location for the glass tag, and reading with various reading devices may be restricted under certain circumstances.

Furthermore, the present disclosure relates to an adapter component for retrofitting a plug socket of a control device, which is configured and provided in such a way that a cable plug, on or in which a glass tag is attached to/in or attachable to/in, can be plugged into it, wherein the adapter component is a ring-shaped element which is attachable/pluggable or attached/plugged to the plug socket, in which an antenna is integrated, which is provided and configured for reading out the glass tag of the cable plug. In other words, the plug socket of future and preferably also previous control devices has a corresponding antenna. This means that a motor cable with a glass tag can be used forward with future and backward with existing control devices. Accordingly, a holder/screen basket receives a corresponding reader antenna so that all application steps in connection with the motor cable can be detected. In other words, this means that existing control devices can be retrofitted with a reader antenna.

In addition, the present disclosure relates to a system comprising a medical instrument, a motor cable, a cable plug having a pole-side end and a cable-side end which is connected to the motor cable and at the end of which an electric motor of a medical device can be supplied with current, and a control device having a plug socket into which the pole-side end can be plugged, wherein a glass tag is arranged at or in the pole-side end, wherein the tag is provided and configured to be readable by an antenna arranged at the plug socket.

In summary, a very compact, simple, space-saving and robust protective housing is provided in which the glass tag is integrated and can be easily retrofitted to the motor cable during servicing. In other words, this protective housing can be integrated into today's motor cable assembly without the need for machining. The motor cable with the glass tag can therefore be used forward with future and backward with existing control devices. Alternatively, it is also possible to retrofit the control device so that the motor cable with the glass tag can also be used forward with existing control devices. In other words, the motor cable can be retrofitted during the annual servicing, if desired and backward-compatible with existing control devices.

BRIEF DESCRIPTION OF THE DRAWINGS

FIG. 1 is a representation illustrating RFID tags that can be used according to the invention;

DETAILED DESCRIPTION

Configuration examples of the present disclosure are described below on the basis of the associated Figures.

FIG. 1 is a representation illustrating glass tags 7 that can be used according to the invention, showing the different sizes of glass tags 7, in particular so-called glass RFID tags, next to a commercially available match. Accordingly, the glass tags 7 have a cylindrical shape with rounded ends, which resembles a rod or pill shape. Such glass tags 7 are essentially state of the art and therefore require no further description. Such a glass tag 7 has a coil that is wound around the center of a rod-shaped ferrite core and is in contact with an RFID chip. The RFID chip is usually placed at one axial end of the ferrite core. This construction consisting of the ferrite core is enclosed by a radio wave permeable material, e.g. a glass material, which forms the housing of the glass tag 7.

Figure 2:
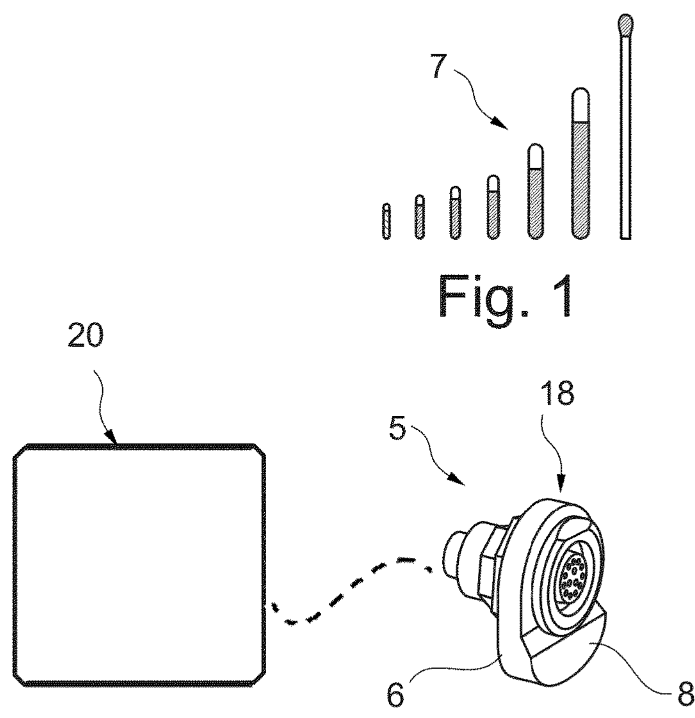
FIG. 2 is a representation illustrating a plug socket of a control device.

FIG. 2 is a representation illustrating a plug socket 5 of a control device 20. The plug socket 5 has a reader antenna 8. The reader antenna 8 is arranged/integrated in a ring 6, which also has a thickening on one side in which the reader antenna 8 is inserted. It is preferred if the ring 6 is configured so that it can be plugged onto the plug socket 5 of the control device 20. This means that the plug sockets 5 of previous control devices 20 can be retrofitted.

The ring 6 and the reader antenna 8 together form an adapter component 18, which is provided for retrofitting the plug socket 5.

First Embodiment

Figure 3:
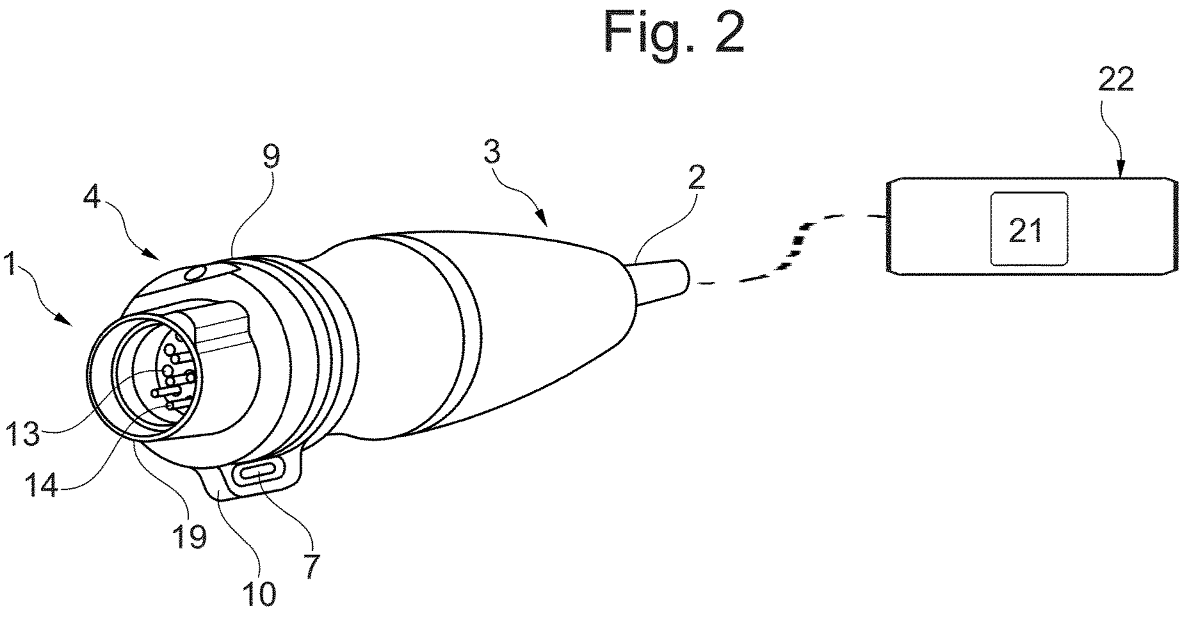
FIG. 3 is a representation illustrating a cable plug according to a first embodiment.

FIG. 3 is a representation illustrating a cable plug 1 according to a first embodiment. The cable plug 1 has a cable-side end 3 and a cable-side end 4. A motor cable 2, which is connected to a medical/surgical instrument 22, is connected to the cable-side end/end portion 3 of the cable plug 1. In other words, the cable 2 shown by way of indication leads to a medical (hand) instrument 22 in which, for example, an electric motor 21 is accommodated for driving a tool (drill, milling cutter, etc.) inserted into the medical/surgical instrument 22. The pole-side end/end portion 4 of the cable plug 1 is configured in the shape of a plug and thus forms a plug-in portion of the cable plug 1. The pole-side end/end portion 4 therefore has a number of plug-in locations 13 on its front side, some of which are provided/equipped with pole plugs 14. The plug-in locations 13 and pole plug 14 are surrounded/enclosed by an annular (preferably metallic) frame 19, which is provided for being plugged into a plug socket 5 according to FIG. 2, for example of an external control device 20.

In a further portion, which connects toward the cable-side end 3 in connection to the ring-shaped frame 19, the cable plug 1 has a thickening which is enclosed/surrounded by a color-coded ring 9. The color-coded ring 9 is configured or provided with a zeppelin cockpit 10 on one side of the cable plug 1. The zeppelin cockpit 10 is a preferably bunker-like or mound-like projection and is large enough to accommodate/integrate a glass tag 7 therein, preferably without tension. The glass tag 7 is arranged in the zeppelin cockpit 10 in such a way that one front side points toward the pole-side end 4. There is a handle between the color-coded ring 9 and the motor cable 2. The zeppelin cockpit 10 can be formed in one piece with the color-coded ring 9 or glued or welded/ soldered to it.

Figure 4:
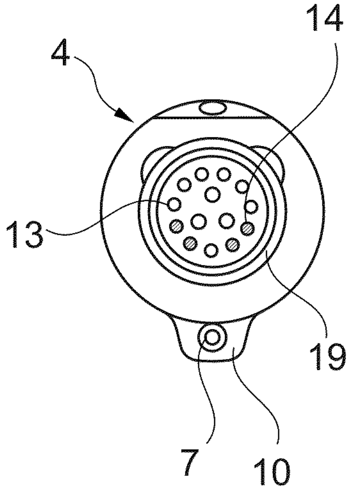
FIG. 4 is a view of a pole-side end of the cable plug according to the first embodiment.

FIG. 4 is a view of a pole-side end/end portion 4 of the cable plug 1 according to the first embodiment. The pole-side end/end portion 4 of the cable plug 1 has a circular basic shape. An annular frame 19 is preferably arranged in the center of the circular basic shape of the cable plug 1. FIG. 4 shows the plug-in locations 13 and pole plug 14 (shown hatched) arranged in the ring-shaped frame 19. In this respect, the plug-in portion resembles a plug on the trailer coupling of a motor vehicle, for example, in terms of its function and basic shape.

On the lower circumferential side/circumferential portion of the circular basic shape as shown in FIG. 4, the zeppelin cockpit 10 is shown, in which the front side of the glass tag 7 inserted in it can also be seen. The zeppelin cockpit 10 extends the circular basic shape in a radial direction in a trapezoidal shape on one side/circumferential portion of the circular basic shape. The zeppelin cockpit 10 is configured large enough to accommodate the glass tag 7 integrally and at the same time to protect it from external influences.

Figure 5:
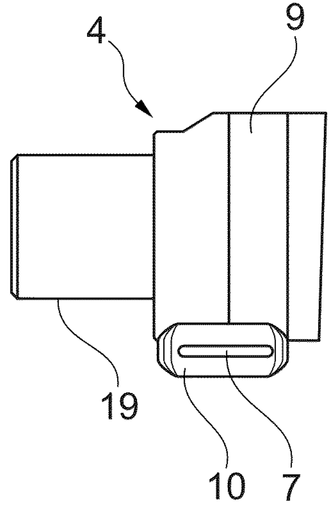
FIG. 5 is a side view of the cable plug according to the first embodiment.

FIG. 5 is a side view of the cable plug 1 according to the first embodiment. In FIG. 5, the ring-shaped frame 19 is shown on the left and the color-coded ring 9 with the zeppelin cockpit 10 is shown on the right, in which the pose of the glass tag 7 is shown. It is shown here that the glass tag 7 is arranged parallel to the longitudinal direction of the cable plug 1 and the zeppelin cockpit 10 is arranged on the outer circumference of the color-coded ring 9.

Figure 6:
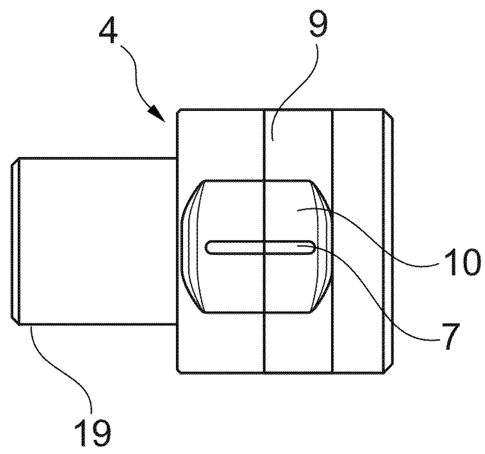
FIG. 6 is a top view of a zeppelin cockpit of the cable plug according to the first embodiment.

FIG. 6 is a top view of the zeppelin cockpit 10 of the cable plug 1 according to the first embodiment. In the top view, the zeppelin cockpit 10 of the cable plug 1 has an octagonal basic shape with the glass tag 7 arranged in the middle. The zeppelin cockpit 10 overlaps with the color-coded ring 9 over the full width of the color-coded ring 9 and protrudes from the color-coded ring 9 in the direction of the pole-side end.

Second Embodiment

Figure 7:
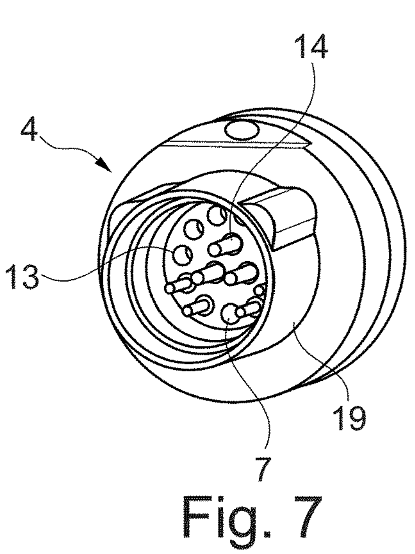
FIG. 7 is a view of the pole-side end of the cable plug according to a second embodiment.

FIG. 7 is a view of the pole-side end/end portion 4 of the cable plug 1 according to a second embodiment. The pole-side end/end portion 4 of the cable plug 1 is configured according to the first embodiment, but with the difference that the glass tag 7 is inserted into a free plug-in location 13. According to FIG. 7, the glass tag 7 is completely/fully recessed in the plug-in location 13. For this purpose, the glass tag is inserted into a cylindrical protective housing, which is dimensioned such that it can occupy the one free plug-in location precisely. In this case, there is no need for an externally visible zeppelin cockpit as in the first embodiment.

Third Embodiment

Figure 8:
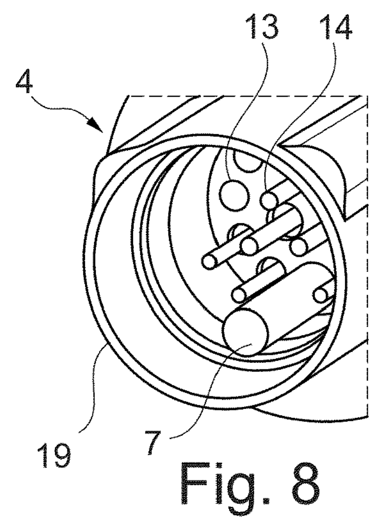
FIG. 8 is a view of the pole-side end of the cable plug according to a third embodiment.

FIG. 8 is a view of the pole-side end/end portion 4 of the cable plug 1 according to a third embodiment. The pole-side end/end portion 4 of the cable plug 1 is also configured according to the first embodiment, with the difference that the glass tag 7 is inserted in a free plug-in location 13. According to FIG. 8, the glass tag 7 is at least partially recessed/inserted in the plug-in location 13 and protrudes axially out of the plug-in location 13, but does not protrude beyond the annular frame 19. In this case too, the glass tag 7 is inserted into a cylindrical protective housing, which is dimensioned in such a way that it can occupy the one free plug-in location 13 precisely.

Figure 9:
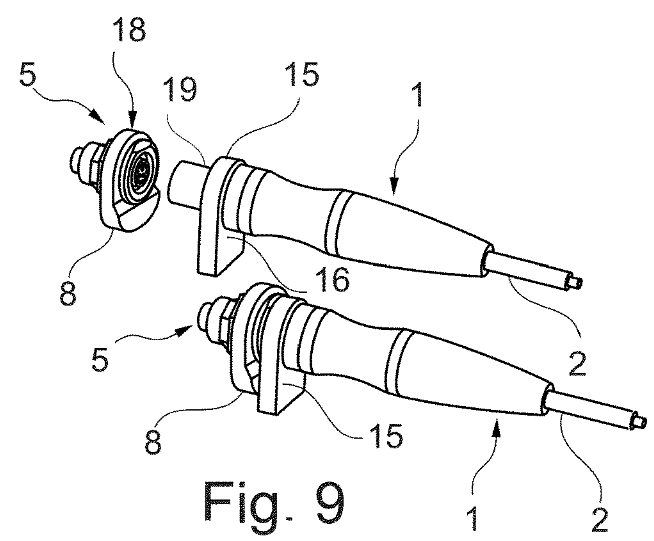
FIG. 9 is a representation of a cable plug according to a fourth embodiment.
Figure 10:
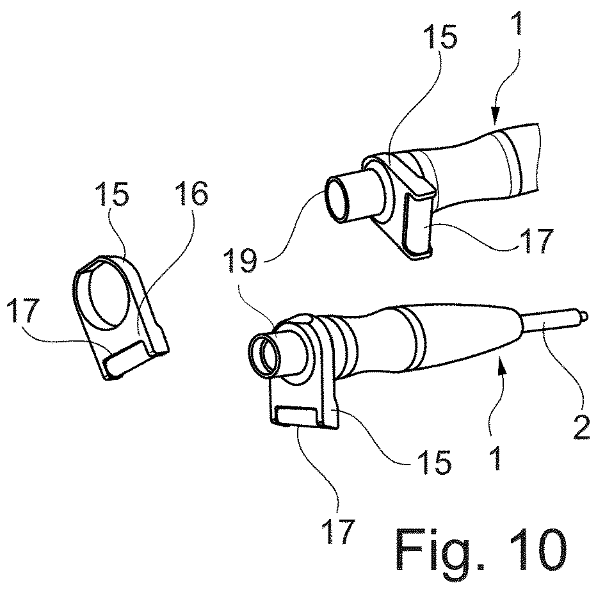
FIG. 10 is a view of the pole-side end of the cable plug according to the fourth embodiment.

FIG. 9 is a representation of a cable plug 1 according to a fourth embodiment. FIG. 10 is a view of the pole-side end/end portion of the cable plug 1 according to the fourth embodiment. FIG. 9 shows the cable plug 1 and the plug socket 5 according to FIG. 2 separated from each other (upper part of FIG. 9) and the cable plug 1 and the plug socket 5 according to FIG. 2 inserted into each other (lower part of FIG. 9). FIG. 10 shows a plug-on ring 15 once and the cable plug 1 twice with the ring 15 attached to it from different side views.

Accordingly, all illustrations of FIGS. 9 and 10 show the cable plug 1 with the plug-on ring 15, which has a rectangular extension 16 in the form of a shield or parrying blade on one half/on one side of the plug-on ring 15. The rectangular extension 16 is configured integrally with the ring 15.

The plug-on ring 15 is configured in such a way that it can be plugged onto the ring-shaped frame 19 and, when the pole-side end 4 of the cable plug 1 is inserted into the plug socket 5 as shown in FIG. 2, is arranged between the plug socket 5 and the thickening of the pole-side end 4. Accordingly, by inserting the cable plug 1 into the control socket 5 of the control device 20, the plug-on ring 15 is fixed on/to the ring-shaped frame 19.

A tag holder 17 is provided at the free end portion of the right kick extension 16. The tag holder 17 is provided and configured to hold the glass tag 7 largely force-free.

Figure 11:
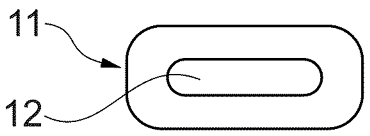
FIG. 11 is a representation of a planar signal amplification plate.
Figure 12:
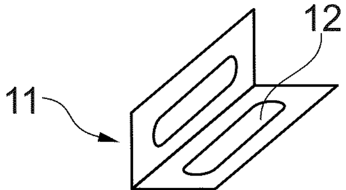
FIG. 12 is a representation of an L-shaped signal amplification plate.
Figure 13:
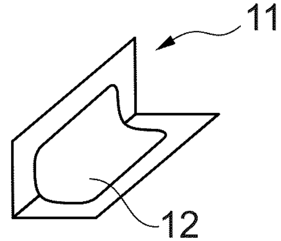
FIG. 13 is another representation of an L-shaped signal amplification plate.
Figure 14:
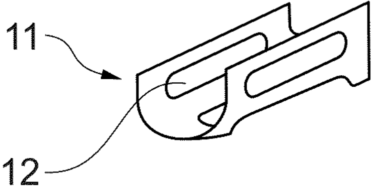
FIG. 14 is a representation of a U-shaped signal amplification plate.

FIGS. 11 to 14 are representations of different embodiments of a signal amplification plate 11. FIG. 11 is a representation of a planar signal amplification plate 11, FIG. 12 is a representation of an L-shaped signal amplification plate 11, FIG. 13 is a further representation of an L-shaped signal amplification plate 11 and FIG. 14 is a representation of a U-shaped signal amplification plate 11.

Accordingly, FIG. 11 shows a flat signal amplification plate 11 in which an opening 12 is provided. The opening 12 is preferably provided in the center of the signal amplification plate 11 and provides the glass tag 7 arranged on or at the signal amplification plate 11 with an effective direction in which the readability of the glass tag 7 is/is improved or enhanced.

FIG. 12 shows an L-shaped signal amplification plate 11, which has two openings 12. An opening 12 is provided in each plane/surface of the L-shaped signal amplification plate 12 and provides the glass tag 7 arranged on/or at the signal amplification plate 11 with an effective direction in which the readability of the glass tag 7 is/is improved or enhanced.

FIG. 13 shows an L-shaped signal amplification plate 11, which has a kinked opening 12. This opening 12 extends over the edge and thus over both planes/surfaces of the L-shaped signal amplification plate 11 and offers the glass tag 7 arranged on/or at the signal amplification plate 11 two effective directions in which the readability of the glass tag 7 is/are improved or amplified.

FIG. 14 shows a U-shaped signal amplification plate 11, which has three openings 12. An opening 12 is provided in each plane/surface of the U-shaped signal amplification plate 12 and provides the glass tag 7 arranged on/or at the signal amplification plate 11 with an effective direction in which the readability of the glass tag 7 is/is improved or enhanced.

Each embodiment can be used in combination with the signal amplification plate 11 shown as an example.

The invention claimed is:

1. A medical instrument comprising:

a medical device with at least one internal electric energy consumer;

a cable plug;

a motor cable; and a glass tag, the motor cable connecting the medical device to a cable-side end of the cable plug for supplying the at least one internal energy consumer, the cable plug comprising a pole-side end for being plugged into a plug socket, the glass tag being attachable in/to or attached in/to the pole-side end without applying force, and the glass tag configured to be readable by an antenna arranged on the plug socket.

2. The medical instrument according to claim 1, wherein the glass tag is arranged in a color-coded ring, wherein the color-coded ring surrounds the cable plug at the pole-side end.

3. The medical instrument according to claim 2, wherein the color-coded ring is configured with a protrusion extending radially outward from the color-coded ring and the glass tag is configured to be integrated into the protrusion.

4. The medical instrument according to claim 1, wherein the glass tag is integrated in a ring which can be plugged onto the pole-side end.

5. The medical instrument according to claim 4, wherein an outer side of one half of the ring has a cuboid extension in which a tag holder is provided and configured, in which the glass tag is held.

6. The medical instrument according to claim 1, wherein the glass tag comprises a signal amplification plate that has at least one opening.

7. The medical instrument according to claim 6, wherein the signal amplification plate is a flat plate, an L-shaped plate, a U-shaped plate or a tubular plate.

8. The medical instrument according to claim 1, wherein the pole-side end has a plurality of plug-in locations, wherein only a part of the plurality of plug-in locations is occupied by pole plugs and the glass tag is inserted at least partially insertably in an unoccupied plug-in location.

9. The medical instrument according to claim 1, wherein the glass tag is configured to be demountable and/or exchangeable without damaging the medical instrument.

10. A system comprising:

a medical instrument;

a motor cable;

a cable plug having a pole-side end and a cable-side end;

a control device; and a glass tag, the cable plug being connected to the motor cable and comprising a cable end, the cable end configured to supply current to an electric motor of a medical device, the control device having a plug socket into which the pole-side end is pluggable, the glass tag being arranged at or in the pole-side end, and the glass tag being configured to be readable by an antenna arranged at the plug socket.

* * * * *